United States Patent
Warnke et al.

(10) Patent No.: US 8,911,147 B2
(45) Date of Patent: Dec. 16, 2014

(54) SYSTEM AND METHOD FOR ANALYZING A THERMAL IMAGE USING CONFIGURABLE MARKERS

(75) Inventors: Stefan H. Warnke, Santa Cruz, CA (US); Thomas Heinke, Santa Cruz, CA (US)

(73) Assignee: Fluke Corporation, Everett, WA (US)

(*) Notice: Subject to any disclaimer, the term of this patent is extended or adjusted under 35 U.S.C. 154(b) by 1973 days.

(21) Appl. No.: 11/812,227

(22) Filed: Jun. 15, 2007

(65) Prior Publication Data

US 2008/0308732 A1 Dec. 18, 2008

(51) Int. Cl.
*G01J 5/00* (2006.01)
*G01K 3/00* (2006.01)
*G01N 25/72* (2006.01)

(52) U.S. Cl.
CPC .................................. *G01N 25/72* (2013.01)
USPC ............ 374/124; 374/120; 374/121; 374/137

(58) Field of Classification Search
USPC .................................. 374/124, 120, 121, 137
See application file for complete search history.

(56) References Cited

U.S. PATENT DOCUMENTS

| | | | | |
|---|---|---|---|---|
| 4,218,707 A | * | 8/1980 | Reed et al. ..................... | 348/164 |
| 4,343,182 A | * | 8/1982 | Pompei ........................... | 374/31 |
| 7,339,685 B2 | * | 3/2008 | Carlson et al. ................. | 356/614 |
| 2004/0071186 A1 | * | 4/2004 | Ignatowicz ..................... | 374/139 |
| 2004/0264542 A1 | * | 12/2004 | Kienitz .......................... | 374/120 |
| 2006/0198421 A1 | * | 9/2006 | Schreher ........................ | 374/121 |
| 2007/0087311 A1 | * | 4/2007 | Garvey et al. .................. | 434/21 |
| 2008/0265162 A1 | * | 10/2008 | Hamrelius et al. ............. | 250/330 |
| 2010/0054545 A1 | * | 3/2010 | Elliott ........................... | 382/115 |

* cited by examiner

*Primary Examiner* — Mirellys Jagan
(74) *Attorney, Agent, or Firm* — Christensen O'Connor Johnson Kindness PLLC (57) ABSTRACT

A graphical user interface for analyzing thermal images is provided. The interface can be used to identify the temperatures at multiple areas of interest defined on an image. The areas can be denoted by configurable markers of different predetermined shapes. In some embodiments, the interface simultaneously displays temperature statistics relating to the user-identified areas of interest.

15 Claims, 9 Drawing Sheets

SYSTEM AND METHOD FOR ANALYZING A THERMAL IMAGE USING CONFIGURABLE MARKERS

TECHNICAL FIELD

The following is related to thermal imaging systems and procedures, and more particularly, to systems and methods for viewing a thermal image and analyzing associated data recorded by thermal image devices.

BACKGROUND

Thermographic imaging systems operate by mapping detected temperatures to the spectrum of visible light. A relatively cold temperature may be displayed as a black or blue color while a relatively hot temperature may be displayed as a red or white color. Thermal imaging instruments are necessary because the human eye cannot perceive temperature directly.

Infrared thermal imaging instruments commonly are used for obtaining temperature profiles of objects such as industrial machines or components of operating equipment. Inspecting an object's operating temperature conditions can reveal whether a failure is imminent or a machinery adjustment is necessary. Portable imagers are particularly useful for inspecting a series of machines along a route in, for example, a factory.

Some known systems include capability for downloading thermal images recorded on the device to a base computer. The base computer can be used to store downloaded images or to view images on a computer screen that is much larger than the user interface provided in a portable thermal imaging device. If a user desires additional information about any given image, known imaging software applications enable the user to select a single image and view it with greater detail.

DETAILED DESCRIPTION

A computer software system and graphical user interface are described that provide improved capabilities for viewing thermal images and analyzing associated data recorded by thermal image devices. This enables users to interpret thermal profiles for a plurality of images more quickly and effectively.

As described above, a thermal imaging instrument can be used in conjunction with imager software installed in a computer system, such as a PC or laptop computer, to organize and track maintenance data. Once a user has captured a series of images on a portable device, the images can be downloaded or otherwise transferred to a host computer. This transfer can be performed via a USB, Firewire, serial, parallel, or other wired or wireless conduit. Images can then be stored on the computer as a collection of images.

Images (and their associated data) in the collection then can be moved into different folders to organize information specific to different groups of equipment, plant areas, departments, etc. Once a thermographic image has been transferred to the host computer, additional analysis can be performed. For example, the interface can be configured to display the temperature of any target point on a thermographic image. A target temperature point can be user-selected using any suitable interface device.

Figure 1:
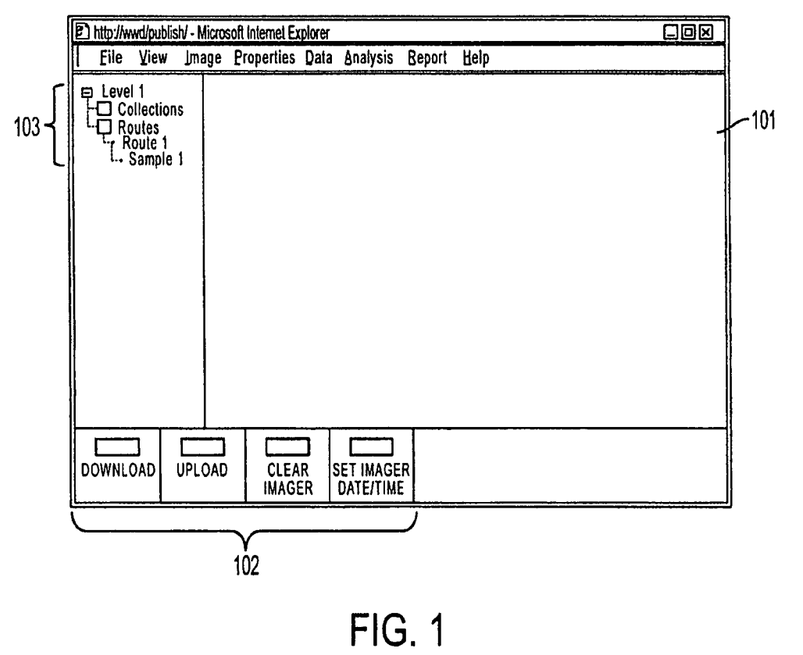
FIG. 1 illustrates an example interface for displaying previously captured image data.

FIG. 1 illustrates an exemplary window configuration for managing downloaded images. As shown, the window configuration can include a pane area (101) for displaying thumbnails of the images. A button area (102) can be provided for displaying functional buttons or icons. A folder view area (103) can be provided for displaying a tree view of folders for storing one or more hierarchical collections of images.

More particularly, the pane area (101) can include a single image or a gallery having multiple images. The images can each be of the same size, or the images can be sized differently. If the number of images in a gallery exceeds the size of the pane area, one or more scroll bars (not shown) can be included on the horizontal and/or vertical axis to enable a user to scroll through the pane area to view different images. Optionally, the "VIEW" selection in the menu bar at the top of the screen can be used to increase or decrease the size of thumbnails displayed in the pane area.

The button area (102) can be used for interfacing with the thermal imager from a personal computer. Since a thermal imager typically is rather compact, with buttons, it is easier to program or control certain aspects of the imager through an associated personal computer. For example, as shown in FIG. 1, by mouse clicking on any of the icons, or "buttons," a user can (i) download image data stored on the thermal imager to the personal computer; (ii) upload images stored on the personal computer into the thermal imager; (iii) clear, or delete all images from the thermal imager; or (iv) program the imager by setting the date and time. Icons can be provided for programming several aspects of the imager's operation.

A folder view area (103) in the exemplary window configuration can be used to organize the storage of image data and other information on the personal computer. At a glance, a user can utilize the folder view area to access, for example, image data from a particular route, or a particular collection of images in a gallery. Upon selecting a folder, thumbnails of images associated with that folder then are displayed in the pane area 101.

Figure 2:
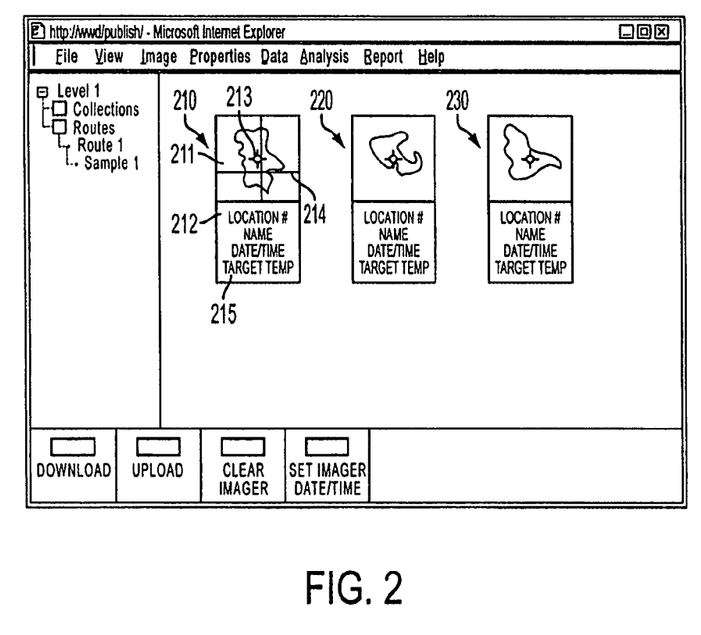
FIG. 2 illustrates the example interface of FIG. 1 displaying multiple thumbnails of images associated with previously captured image data.

FIG. 2 illustrates the exemplary window configuration of FIG. 1, populated with thumbnails of images. As can be seen, in pane area (101) there is shown three thumbnails (210, 220, 230), which each include an image region (211, 221, 231) and a text information region (212, 222, 232). Image region (211) includes a central crosshair (213), indicating the target temperature at the center of the image, and a user-selectable crosshair (214), indicating the temperature of the image at the point of intersection of the crosshair. Considering that a thermal instrument user typically aims the imager so that the center of the image captures the area of interest, the central crosshair (213) provides a useful indication of the temperature associated with the image. The temperature at that point is referred to as the "Target Temperature," and is indicated in the text information region (212) at the bottom row of text (215). The text information region (212) also includes text for indicating a location number, location name, and date/time that the image data was captured. Other information can be included as well.

By including information for a grouping of images in a gallery format, a user can quickly and easily review several images, simultaneously. If the image grouping corresponds to image captures of the same object over a period of time, the user can easily detect trending. For example, if it can be seen that a certain component within a machine is becoming increasing hot, the user may discern that the component is failing and needs to be replaced. If the image grouping corresponds to a route, the user can easily detect at a glance whether there appear to be any problems on the day that the route occurred.

Although the thumbnails described are typically sufficiently detailed to enable the viewer to recognize the subject of the image, the viewer often desires or needs to view the image at full size to appreciate the detail conveyed by the image data. Often, the thumbnail displayed incorporates less than the full resolution of the original acquired image.

Figure 3:
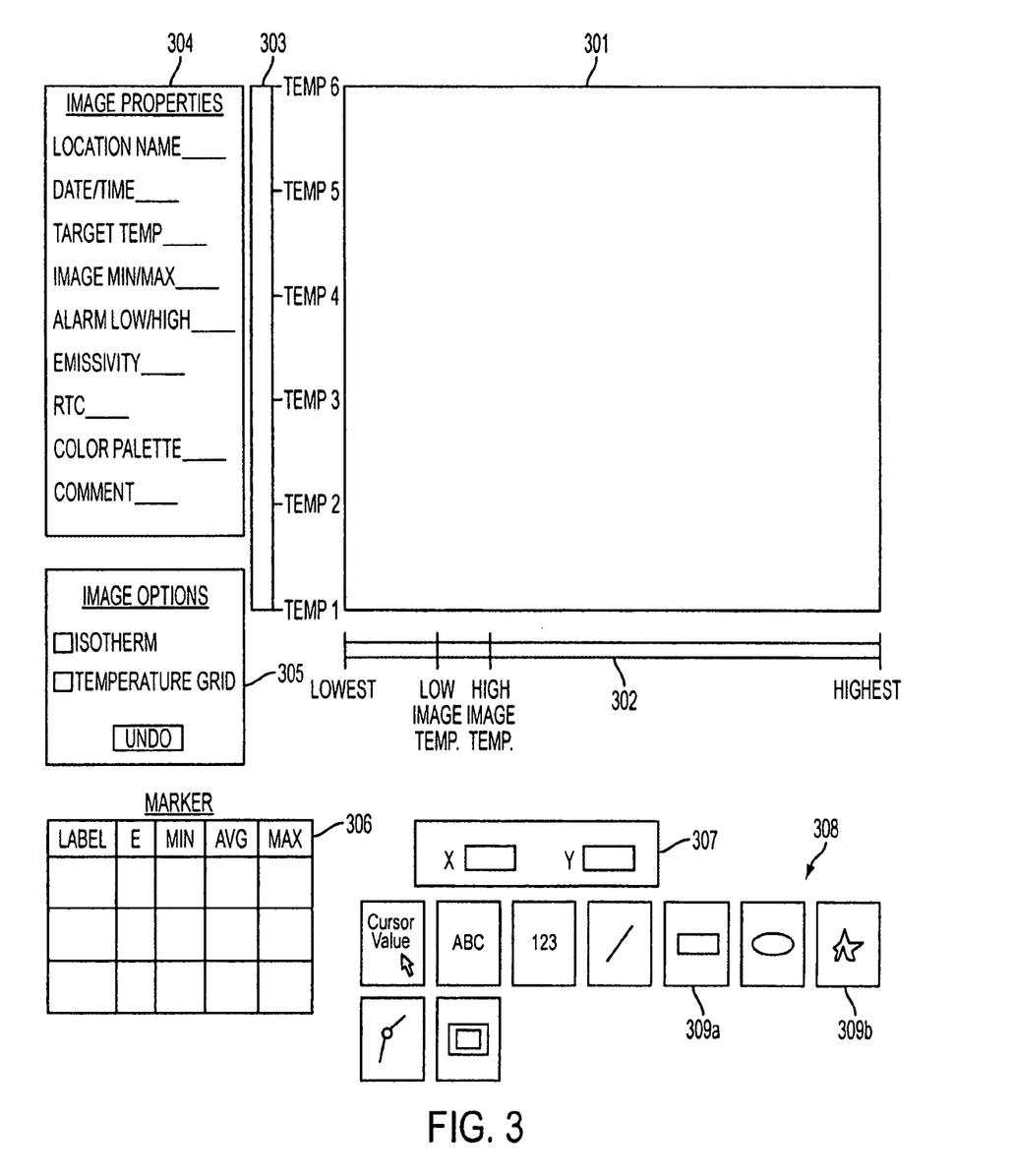
FIG. 3 illustrates an example interface for displaying a detail view of a single thumbnail associated with previously captured image data.

FIG. 3 illustrates an exemplary window configuration for viewing and analyzing a single image in a full-view. In an exemplary embodiment, a user enters this screen upon selecting a thumbnail to view at a full size. This can be done by mouse clicking on a part of the thumbnail image (such as the text information region 212). Alternatively, a user can access a full image by selecting an image and using the menu bar along the top of the window.

As can be seen, an image pane (301) is provided for viewing a single image. Below the image pane, a range bar (302) is provided for illustrating where the temperature range of the image falls in the overall capability of the instrument. A color range bar (303) assigns colors (not shown) to the range of temperatures illustrated in the image pane (301). As an example, if the range bar (302) shows that the temperatures in the image pane range from 20° C. to 50° C., where "low image temp" is 20° C. and "high image temp" is 50° C., then in the color range bar (303), a colorwash of temperatures would be shown as a temperature gradient between the "low image temp" and the "high image temp."

IMAGE PROPERTIES section (304) provides text information relating to the displayed image. In an exemplary embodiment, this section includes the LOCATION NAME (a user-provided name of for the image), LOCATION NUMBER (another identifier for the image), DATE/TIME (when the image was captured), and TARGET TEMP (the temperature at the center of the image). The TARGET TEMP value corresponds with the data in the text information region associated with thumbnails in the gallery view described with reference to FIGS. 1 and 2. As shown in FIG. 3, the IMAGE PROPERTIES (304) section additionally may include IMAGE MIN/MAX values, corresponding to the lowest image temperature and the highest image temperature in the image pane (301). ALARM HIGH/LOW values may be included, corresponding to the alarm values that the user set in the imager when capturing the image (or at sometime beforehand, when configuring the instrument). EMISSIVITY and RTC values can be provided, and can be adjustable. Additionally, the user can select a COLOR PALETTE, which changes the actual color scheme associated with the temperatures according to user preferences. A COMMENT section also can be provided, in which a user can enter comments (in sentence form if desired) to indicate any problems, clearances, or to note any potential warning indicators.

The window configuration can additionally include an IMAGE OPTIONS section (305), which provides selectable options to re-format the image displayed in the image pane (301). For example, a user can opt to display the image data in an Isotherm or with a Temperature Grid. Particularly, the Temperature Grid can be used in conjunction with the COMMENT section to enable the user to better describe and identify a problem area.

A geographical coordinates section 307 also may be provided. This section can be used to identify the cursor coordinates as it is placed by a mouse across the image pane (301).

In accordance with embodiments of the invention, the window configuration may additionally include a MARKER section (306), as illustrated in FIG. 3. A marker can be any designation, such as a single point, a line, or a geometric area, that a user overlays upon a thermal image on the image pane (301). The marker can be used as a user-defined point of reference on the thermal image. In exemplary embodiments to be described below, a user can define multiple markers and place them upon the image as desired. The markers can be defined to be different geometric shapes and sizes, to enable a user to designate and assess a specific area of interest in the image area. Additionally, information concerning the designated area defined by the marker (within the geometric area) can be displayed in the MARKER section (306) or overlaid on the image itself.

As described earlier, a thumbnail and a full image may automatically include a target temperature, which provides the temperature at the center point of the image. The spot on the image corresponding to the target temperature can be designated on the image (whether in a thumbnail or a full-sized image) by a cross-hair. As illustrated in figures and described below, the markers can be used in addition to the target temperature to identify a temperature at either another point on the image or within a user-specified geometric area on the image.

Returning to FIG. 3, in an exemplary embodiment, the MARKER section can be a chart or table that organizes a listing of markers associated with a thermal image. In the illustrated example, the table may include several columns. LABEL associates a name with the marker. E provides the emissivity. For markers that are defined as geometric areas, MIN provides the minimum temperature within the region, MAX provides the highest temperature in that region, and AVG provides the temperature in the region. Other columns may be included in the chart and additional information pertaining to a marker can be associated with the marker without departing from the scope of the invention. For example, the MARKER section might include the date by which the marker was created, an identification of who created the marker, or an image name or number associated with the marker. In a further embodiment, the marker may be associated with other images in which the same marker is being used.

In FIG. 3, the MARKER section is associated with the set of marker icons (308) corresponding to various marker configuration types for creating a marker. For example, the "ABC" icon can be used to add a text marker at a user-selectable point on the image. If a user mouse clicks on that icon and then clicks on a point on the image, text will be placed on the image. The text can be chosen by the user (e.g., "Piston assembly") so that the user can "flag" a certain aspect of a machine within the image. The marker identifier name or number will also appear in the chart in the MARKER section (306).

As an example of another marker type, if the rectangle icon is selected, the user can find a desired area on the image to place the rectangle, and then define the size of the rectangle. A name or number will then be associated with that marker, as well as temperature information associated with the geographic area defined by the marker. The geographic area corresponds to a two-dimensional array of pixels on the image panel (301). This information can be overlaid within the image itself on image panel (301) and also presented in the chart within MARKER section (306).

Figure 4:
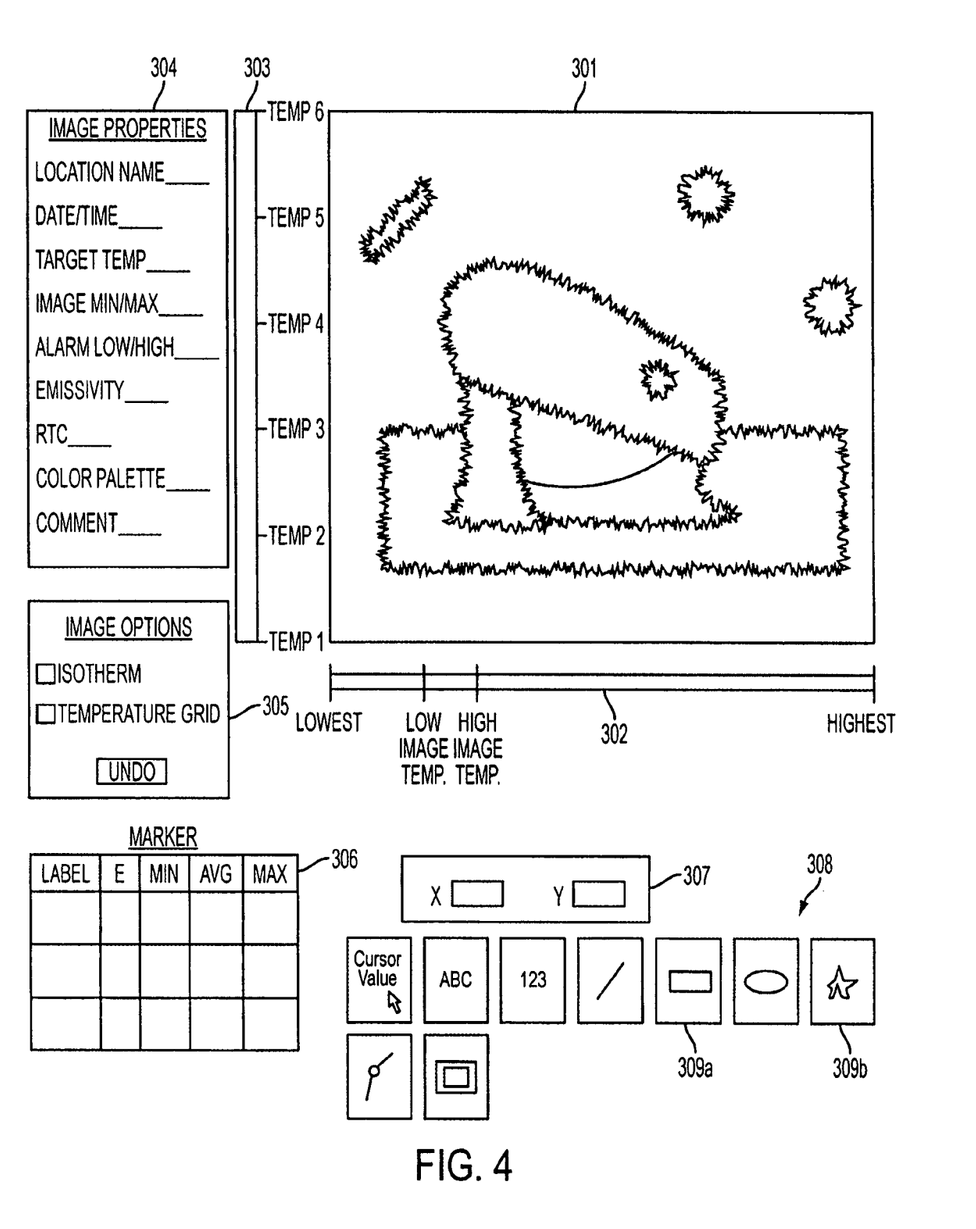
FIG. 4 illustrates the example interface of FIG. 3 displaying a detailed thermal image.

FIG. 4 illustrates the graphical window configuration of FIG. 3 with a thermal image displayed within image pane (301). Of course, on an actual screen, the depicted thermal image would be shown in different colors corresponding to the various associated temperatures according to the temperature range bars (302) and (303). Therefore, the "fuzzy" lines within the image would actually appear as one color fading into another at temperature boundary areas. If a mouse cursor were moved about the image, the x-y coordinates (307) would change to reflect the change in coordinates.

In FIG. 4, the IMAGE PROPERTIES section (304) is automatically populated with information corresponding to the image data associated with the image in the pane area (301). For example, the DATE/TIME field corresponds to the date and time that the displayed image was captured by the imager (which was configured by the personal computer using icon SET IMAGER DATE/TIME (102), described above with reference to FIG. 1). The TARGET TEMP corresponds to the temperature at the center of the image (which may be demarcated by a cross-hair at the center point in the image). The IMAGE MIN/MAX measurements correspond to the low image temperature and the high image temperature.

Figure 5:
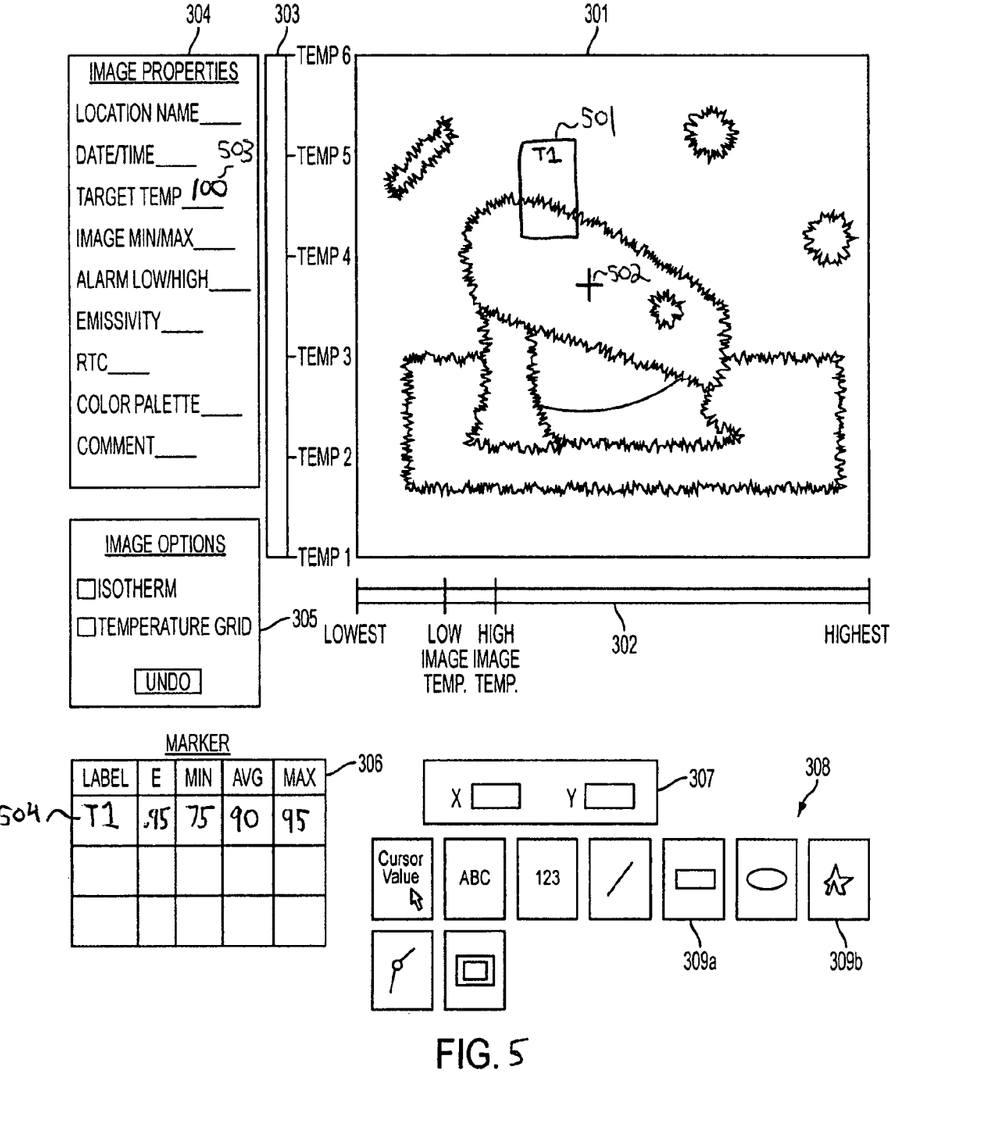
FIG. 5 illustrates the example interface of FIG. 4 displaying a configurable marker superimposed on the image and associated image data in a MARKER table.

FIG. 5 illustrates the graphical window configuration of FIG. 4 with a marker provided on the image. In this figure, a rectangular marker (501) appears on the thermal image in image pane (301). A user places the rectangular marker (501) on the thermal image by selecting the rectangular marker type (309a), and using a mouse to indicate the size and location of the marker. As shown in the figure, the marker is utilized to learn temperature information concerning a particular area of interest within the image. The area of interest is defined by the boundaries of the user-defined rectangular polygon, and includes all of the pixels within the bounded area as a two-dimensional array of pixels. The user can mouse click to indicate the location of the marker upon the image, and then perform a "mouse drag" operation to configure the size of the marker. In an exemplary embodiment, the user can move the marker to adjust its position relative to the image after the marker has been created.

Once the marker is placed upon the image, in an exemplary embodiment, a label, name or identifier associated with the marker is placed within the marker on the image. In this exemplary embodiment, if the marker size is too small to accommodate this information, the label can be placed beside, below, or atop the marker. In FIG. 5, the marker (501) is labeled "T1."

The marker (501) label is also associated with the MARKER table (306). As can be seen, the MARKER table now includes a row of information (504) corresponding to marker T1 (501). In an exemplary embodiment, the MARKER table includes the emissivity, and a minimum, maximum, and average temperature within the area of interest defined by the rectangular marker (501). In FIG. 5, marker (501) appears to bridge a gradient between two temperatures, such that the minimum temperature (MIN) is significantly cooler than the maximum temperature (MAX) within the area of interest.

FIG. 5 also shows a cross-hair (502) that provides a target temperature for the image itself. This target temperature value (503) is provided in the IMAGE PROPERTIES (304). As can be seen, the target temperature may be different from the temperatures in the area of interest within the image. Accordingly, it is advantageous to utilize configurable markers so as to discern particular temperature information concerning temperature data associated with a small portion of the image.

Figure 6:
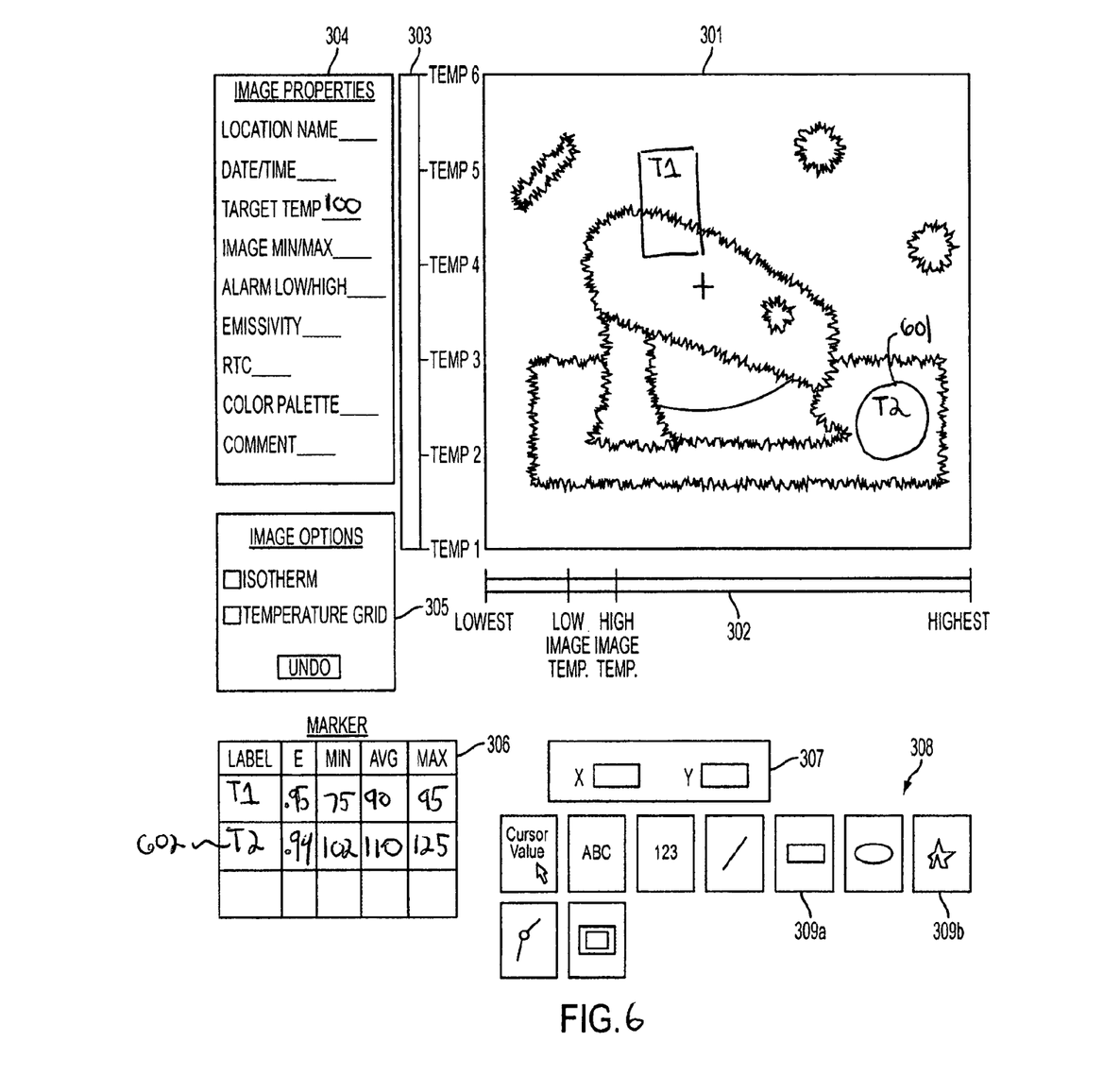
FIG. 6 illustrates the example interface of FIG. 5 displaying multiple configurable markers superimposed on the image and associated image data in a MARKER table.

FIG. 6 illustrates the window configuration of FIG. 5, but with a second marker T2 (601) added thereto. In this manner, two markers, T1 and T2 are provided upon the image, by being superimposed on the image. In this example, marker (601) is selected from the circle shaped marker (308), and is superimposed on the image within image pane (301) in a similar manner as described with regard to marker T1. Again, marker T2 is defined by the circular boundary as depicted in the figure, and corresponds to a two-dimensional array of pixels that are bound by the defined circle shape and the defined size. Referring to MARKER table (602), it can be seen that the particular temperature information associated with marker (602) is provided automatically as a second entry in the table. Specifically, each pixel within the marker's boundary is associated with a temperature value. T2 appears in the LABEL column, and new MIN, AVG, and MAX temperature values are provided that correspond to the pixels in this selected area of interest.

The computer upon which the graphical user interface described above runs performs processing to determine the MIN, AVG and MAX values provided in the MARKER chart (306). As described above, the thermal image in the image pane (301) is created based upon a series of thermal image data downloaded from a thermal imager. To determine the MIN value for T1, for example, the processor evaluates all of the temperature data associated with the two-dimensional pixels within the area of interest defined by the marker, and determines which temperature value is the lowest. As another example, to determine the AVG value for T1, the processor averages all of the temperature data associated with the two-dimensional pixels within the area of interest defined by the marker. In this manner, the graphical user interface can provide a user with particular temperature information corresponding to certain areas of interest within an image pane, to allow for more precise and robust image analysis. This is particularly significant for a user when the area of interest does not correspond to the center point of the image associated with the "target temperature." This feature is also particularly useful when a user is interested in analyzing a particular area within the image. By selecting among a plurality of predetermined shapes (e.g., line, rectangle, oval, multi-point polygon, etc.) the user can select a marker type that will enable the user to most accurate define the area of interest within the thermal image.

Figure 7:
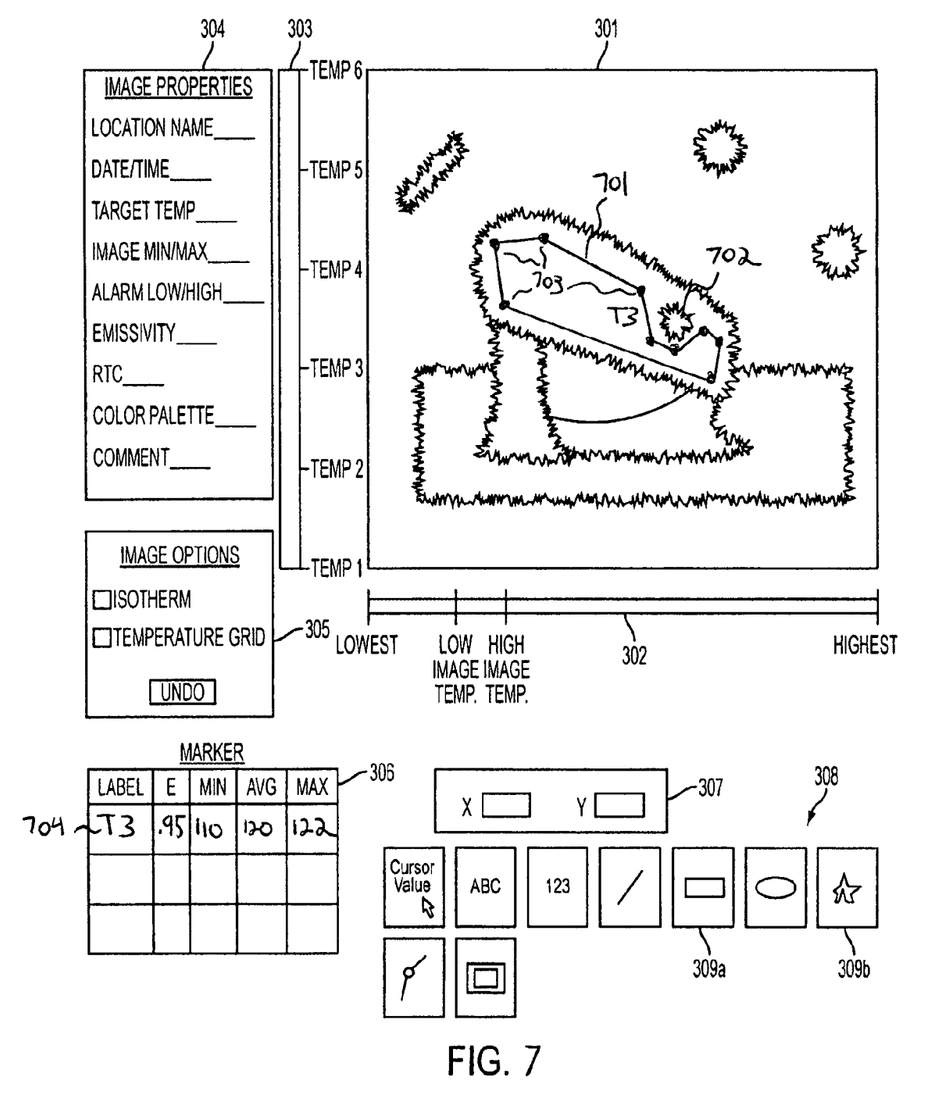
FIG. 7 illustrates the example interface of FIG. 4 displaying a multi-point configurable marker polygon superimposed on the image and associated image data in a MARKER table.

FIG. 7 illustrates a selection of another polygon marker shape in accordance with an exemplary embodiment. As can be seen in image pane (301), marker (701) has been configured so as to capture an area of interest while avoiding a particular area (702). The marker is defined by a user by selecting marker shape (309b) from the marker selection area (308) and placing a series of points (703) upon the image by a series of mouse clicks. The marker (701) is identified as T3, both within the image itself, and in MARKER table (306), where temperature information associated with the marker is provided in row (704).

Figure 8:
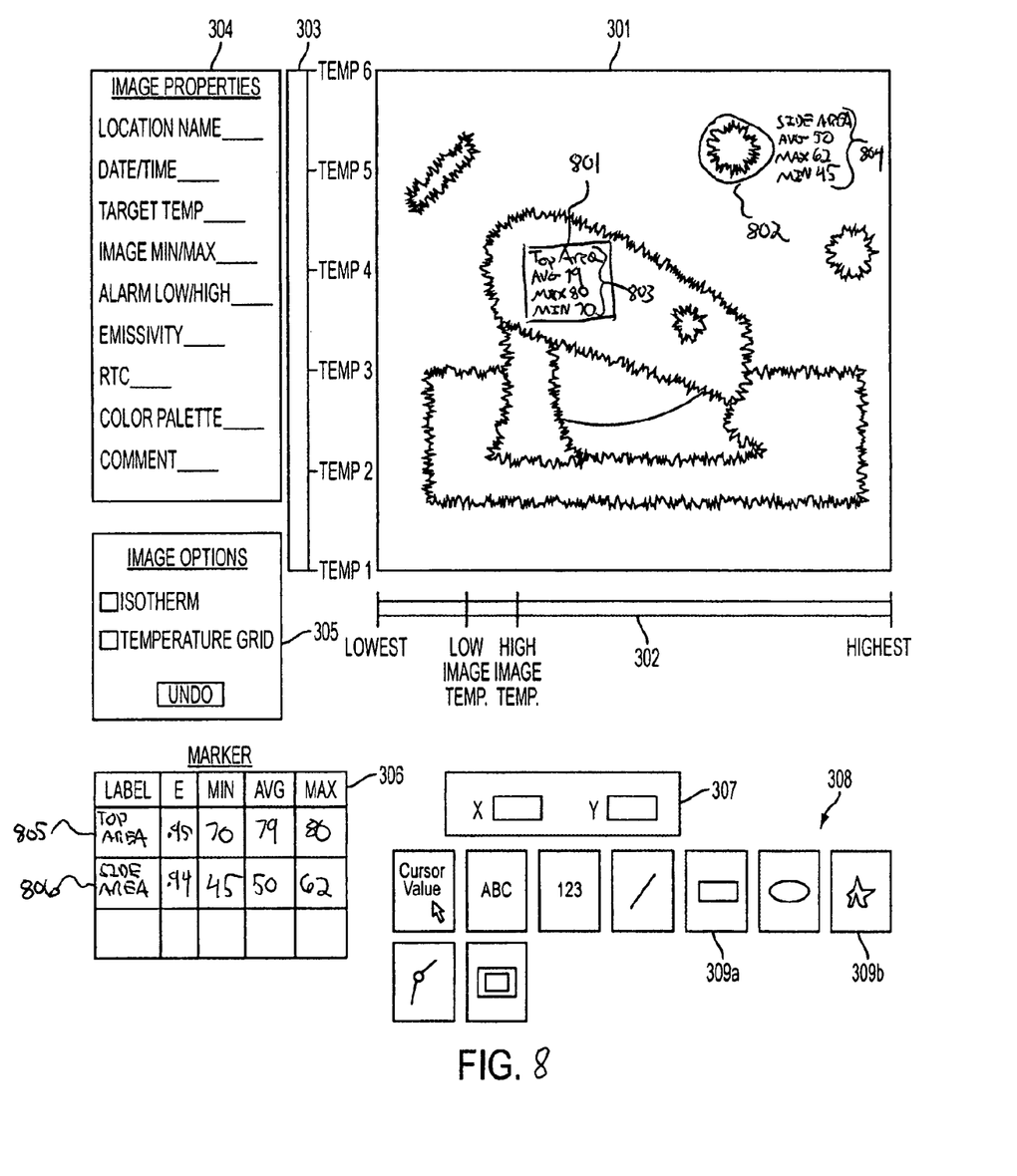
FIG. 8 illustrates the example interface of FIG. 4 displaying multiple configurable markers superimposed on the image and associated image data in or near the markers and in a MARKER table.

FIG. 8 provides another example of the placement of multiple markers upon an image within an image pane (301). In this example, marker (801) defines an area of interest that is of sufficient size and shape to accommodate text corresponding to the associated temperature data (803). Accordingly, the temperature data and marker label is depicted in the image pane as being within the marker boundaries. In contrast, marker (802) defines a comparatively smaller area of interest that is of insufficient size and shape to accommodate text corresponding to the associated temperature data (802). In the exemplary embodiment, the marker label and associated temperature data is placed beside the marker, overlaying the image within image pane (301).

Continuing with FIG. 8, utilizing MARKER table (306), a user can access the LABEL column to change the label associated with a defined marker. In this regard, the label corresponding to marker (801) is provided in row (805), which has been named by a user as "TOP AREA." Once this relabeling occurs, the marker (801) can be relabeled within the text area (803) within the image as well.

In addition to defining polygon-type markers such as a square, rectangle, or user-defined shape (309*b*), the user can create a marker comprised of either a single straight line or a multi-point line, as shown in the icon section (308). This may be useful if a user desires to learn MIN, AVG and MAX temperature statistics corresponding to a straight, curved, or jagged boundary line depicted on an image in the image panel (301). By defining the line, the system can discern the MIN, AVG and MAX temperature values associated with the plurality of pixels defined by the line area.

In addition to using a marker to define an area of interest, a user can also define a point of interest on the image. A user can select a marker type in section (308) that corresponds to marking a single point on the image. Then, upon clicking on a point at a desired location on the image within the image pane (301), a marker indication is provided on the image at that point (not shown), and a temperature value and a label appear above, below, or beside the user-designated point. The associated information may also then be displayed in MARKER table (306), and the label for the designated point can be changed by typing in a new name or identifying number in the LABEL column in row corresponding to the marker in the MARKER table (306). Of course, since the point marker designates a single point, there are not distinct MIN, AVG, and MAX values. Accordingly, in an exemplary embodiment as shown in the figures, only the AVG column is populated with a temperature value corresponding to the temperature at the defined point on the image. A user can select any number of points to include upon the image to identify a plurality of points (each corresponding to a pixel on the image).

Figure 9:
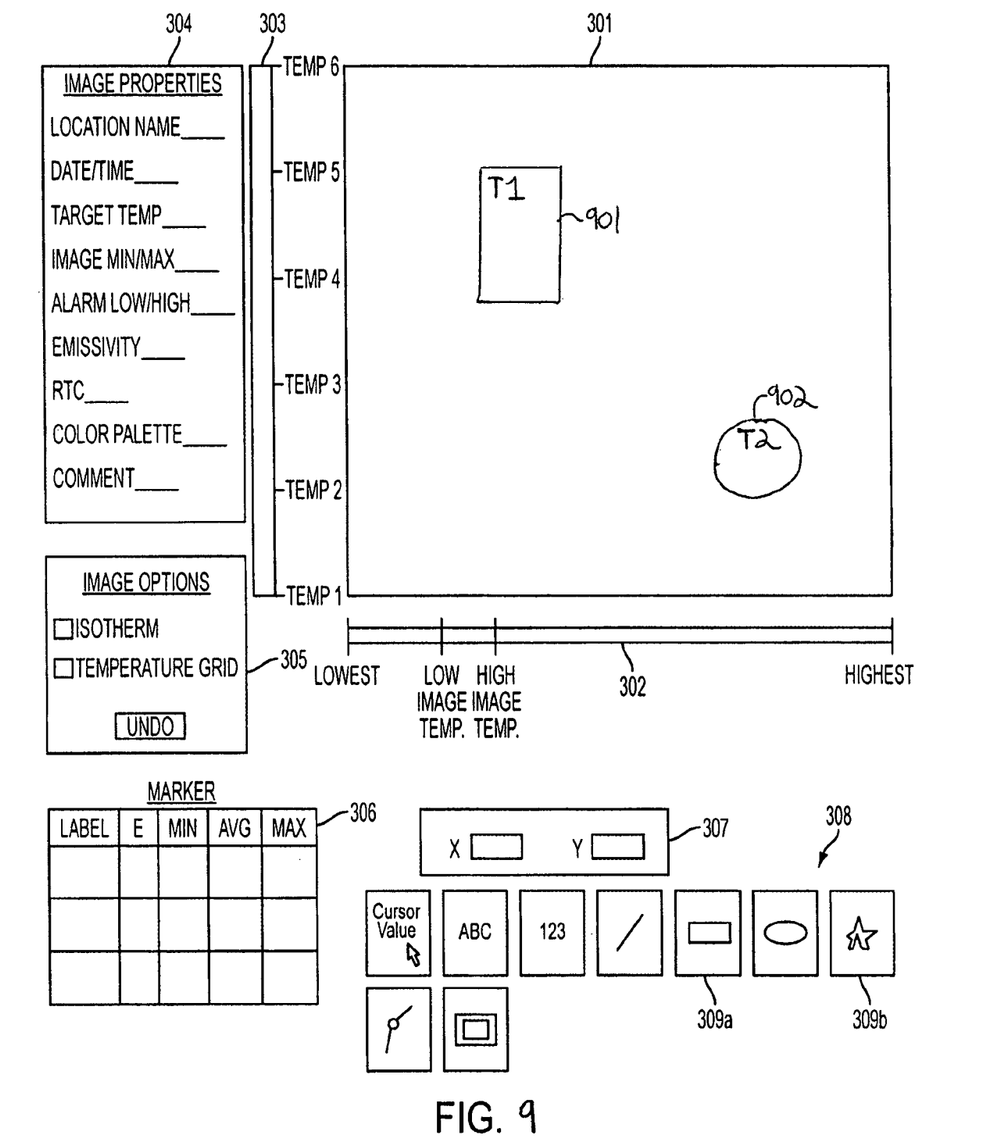
FIG. 9 illustrates the example interface of FIG. 3 displaying a user-defined template having one or more configurable markers.

Referring once more to FIG. 6, in an additional exemplary embodiment, markers T1 and T2 can be saved separately from the image itself to be used as a template to apply to other images. As shown in FIG. 9, markers T1 (901) and T2 (902) have been separated from the image shown in FIG. 6 and can be saved as a template. This template can be stored as a file associated with image analysis software or as a macro or any other data format to insert or apply to other images. In this example, the markers T1 and T2 can then be applied to a completely different thermal image. Notably, when the imaging software is used for analyzing images gathered by performing a route or from another manner in which images of a same machine, tool, motor, or other object are taken at various times, dates, etc., to analyze trends or variations over time, the same markers may need to be used to analyze similar temperature areas of interest within the image. Instead of re-creating the markers, a template can be saved and later applied to a different image so as to overlay subsequent images. In an exemplary embodiment, a user can then utilize a mouse to move or re-define the size or shape of the markers and adjust them to account for slight differences in the different image. For example, a subsequent image may be taken from a slightly different distance from an object, or a slightly different height or other perspective. Like the markers themselves, a template can be associated with a name (e.g., "Air Conditioner Template") to associate the template with a type of image to which it may be applied.

The embodiments can be practiced upon a single computer, or on distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the interface described below may be stored or distributed on computer-readable media, including magnetic and optically readable and removable computer discs, stored as firmware in chips (e.g., EEPROM chips), as well as distributed electronically over the Internet or over other networks (including wireless networks). Those skilled in the relevant art will recognize that portions of the interface may reside on a server computer, while corresponding portions reside on a client computer. Data structures and transmission of data particular to aspects of the interface are also encompassed within the scope of the disclosure.

One embodiment of the interface employs a base computer, such as a personal computer or workstation, having one or more processors coupled to one or more user input devices (e.g., a thermal imager, a mouse or tablet, and a keyboard) and data storage devices. The computer is also coupled to at least one output device such as a display device and one or more optional additional output devices (e.g., printer, plotter, speakers, tactile or olfactory output devices, etc.). The computer may be coupled to external computers, such as via an optional network connection, a wireless transceiver, or both. The base computer can be in electronic communication with a portable imager so that data can be transferred between the base computer and imager. The transfer of data can be performed via a USB, Firewire, serial, parallel, or other wired or wireless conduit.

The input devices may include a keyboard and/or a pointing device such as a mouse. Other input devices are possible such as a microphone, joystick, pen, game pad, scanner, digital camera, video camera, and the like. The data storage devices may include any type of computer-readable media that can store data accessible by the computer, such as magnetic hard and floppy disk drives, optical disk drives, magnetic cassettes, tape drives, flash memory cards, digital video disks (DVDs), RAMs, ROMs, smart cards, etc. Indeed, any medium for storing or transmitting computer-readable instructions and data may be employed, including a connection port to or node on a network such as a local area network (LAN), wide area network (WAN) or the Internet (not shown in FIG. 1).

Aspects of the interface may be practiced in a variety of other computing environments. User computers may include other program modules such as an operating system, one or more application programs (e.g., word processing or spread sheet applications), and the like. The computers may be general-purpose devices that can be programmed to run various types of applications, or they may be single-purpose devices optimized or limited to a particular function or class of functions. Any application program for providing a graphical user interface to a user may be employed.

Many specific details of certain embodiments of the invention are set forth in the description and in the figures to provide a thorough understanding of these embodiments. A person skilled in the art, however, will understand that the invention may be practiced without several of these details or additional details can be added to the invention. Well-known structures and functions have not been shown or described in detail to avoid unnecessarily obscuring the description of the embodiments of the invention.

From the foregoing, it will be appreciated that specific embodiments of the invention have been described herein for purposes of illustration, but that various modifications may be made without deviating from the invention. Aspects of the invention described in the context of particular embodiments may be combined or eliminated in other embodiments. Further, while advantages associated with certain embodiments of the invention have been described in the context of those embodiments, other embodiments may also exhibit such advantages, and not all embodiments need necessarily exhibit such advantages to fall within the scope of the invention.

We claim:

1. A method for identifying temperature data associated with a thermal image, comprising:
    displaying a thermal image stored in a memory on a user interface, the image comprising a two dimensional array of pixels;
    receiving a marker drawn on the displayed thermal image by a user using a drawing tool to create a shape that defines an area of interest of the image;
    calculating at least one temperature statistic associated with the defined area of interest;
    displaying the at least one temperature statistic on the user interface;
    storing a definition of at least one area of interest as a template; and
    applying the template to a plurality of thermal images.

2. The method of claim 1, wherein the marker defining the area of interest comprises a configurable marker.

3. The method of claim 1, wherein the area of interest is defined by a polygon shape drawn on the displayed thermal image.

4. The method of claim 1, wherein displaying the at least one temperature statistic includes displaying at least one of a minimum, maximum, and average temperature value of the area of interest.

5. The method of claim 1, further comprising:
    receiving from the user a label relating to the at least one defined area of interest; and
    displaying the label in association with the at least one temperature statistic calculated for the at least one defined area of interest.

6. The method of claim 1, further comprising displaying on the user interface a plurality of tools for drawing the marker on the displayed thermal image.

7. The method of claim 6, wherein at least one of the plurality of tools provides at least one predetermined shape having a configurable size.

8. The method of claim 1, further comprising:
    receiving additional markers drawn on the displayed thermal image by the user to define additional areas of interest of the image; and
    displaying temperature statistics associated with individual defined areas of interest.

9. The method of claim 8, further comprising displaying the temperature statistics in a table on the user interface simultaneously with the displayed thermal image on the user interface.

10. A computer-readable memory in which a program code identifies temperature data associated with a thermal image, comprising:
    a program code for displaying on a user interface a thermal image stored in the memory, the image comprising a two dimensional array of pixels;
    a program code for receiving a marker drawn on the displayed thermal image by a user using a drawing tool to create a shape that defines an area of interest of the image;
    a program code for calculating at least one temperature statistic associated with the defined area of interest;
    a program code for displaying the at least one temperature statistic on the user interface;
    a program code for storing a definition of at least one area of interest as a template; and
    a program code for applying the template to a plurality of thermal images.

11. The computer-readable memory of claim 10, wherein the area of interest is defined by a configurable marker.

12. The computer-readable memory of claim 10, further comprising a program code for receiving input from the user identifying a size of the marker defining the area of interest.

13. A system for identifying temperature data associated with a thermal image, comprising:
    a display interface for displaying a thermal image stored in a memory, the image including a two dimensional array of pixels; and
    a processor for receiving a marker drawn on the displayed thermal image by a user using a drawing tool to create a shape that defines an area of interest of the image, for calculating at least one temperature statistic associated with the area of interest, for storing a definition of at least one area of interest as a template, and for applying the template to a plurality of thermal images;
    wherein the at least one temperature statistic is displayed on the display interface.

14. The system of claim 13, wherein the marker defining the area of interest comprises a configurable marker.

15. The system of claim 13, wherein the processor receives input from the user identifying a size of the marker defining the area of interest.

* * * * *